(12) United States Patent
Morii et al.

(10) Patent No.: US 7,358,384 B2
(45) Date of Patent: Apr. 15, 2008

(54) PROCESSES FOR THE RECOVERY OF OPTICALLY ACTIVE DIACYLTARTARIC ACIDS

(75) Inventors: Seiji Morii, Nagoya (JP); Toshihiro Fujino, Kuwana (JP); Haruyo Sato, Nagoya (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 10/542,498

(22) PCT Filed: Dec. 22, 2003

(86) PCT No.: PCT/JP03/16474

§ 371 (c)(1),
(2), (4) Date: Jul. 15, 2005

(87) PCT Pub. No.: WO2004/063141

PCT Pub. Date: Jul. 29, 2004

(65) Prior Publication Data

US 2006/0058546 A1    Mar. 16, 2006

(30) Foreign Application Priority Data

Jan. 16, 2003   (JP) .............................. 2003-008023

(51) Int. Cl.
C07C 69/76   (2006.01)
C07C 69/66   (2006.01)
C07C 51/42   (2006.01)
C07C 59/255  (2006.01)

(52) U.S. Cl. .................... 560/66; 560/180; 562/585; 562/580

(58) Field of Classification Search .................. 560/66, 560/180; 562/580, 585
See application file for complete search history.

(56) References Cited

U.S. PATENT DOCUMENTS 6,462,229 B1   10/2002   Meul

FOREIGN PATENT DOCUMENTS

| JP | 6-70063 | 9/1994 |
| JP | 09 176115 A2 | 7/1997 |
| JP | 2712669 | 10/1997 |
| JP | 2917495 | 4/1999 |
| WO | WO 00/17143 | 3/2000 |
| WO | 03/042132 A1 | 5/2003 |

*Primary Examiner*—Taylor Victor Oh
(74) *Attorney, Agent, or Firm*—DLA Piper US LLP

(57) ABSTRACT

When a salt of an amine and an optically active diacyltartaric acid, or a diastereomer salt of an optically active amine and an optically active diacyltartaric acid, obtained by optically resolving a racemic amine using the optically active diacyltartaric acid, is salt-exchanged with an acid aqueous solution, the optically active diacyltartaric acid is added in the acid aqueous solution beforehand.

Furthermore, a raw material containing a racemic amine and an optically active diacyltartaric acid is optically resolved, and the diastereomer salt of the optically active amine and the optically active diacyltartaric acid respectively of one isomer type, is separated. The obtained diastereomer salt is dissociated using an acid aqueous solution containing the optically active diacyltartaric acid, for recovering the optically active diacyltartaric acid, and the obtained optically active diacyltartaric acid is recycled into an optical resolution step as a raw material of the optical resolution step.

25 Claims, No Drawings

PROCESSES FOR THE RECOVERY OF OPTICALLY ACTIVE DIACYLTARTARIC ACIDS

TECHNICAL FIELD

This disclosure relates to a process for recovering an optically active diacyltartaric acid by dissociating a salt of an amine and the optically active diacyltartaric acid.

BACKGROUND

Optically active diacyltartaric acids are compounds important as optical resolving agents for producing optically active amines important as raw materials of medicines. Recovering an optically active diacyltartaric acid from a diastereomer salt obtained in an optical resolution step, for recycled use of it, is essential for constructing a resource-saving industrial process. As processes for recovering an optically active diacyltartaric acid by dissociating a diastereomer salt of an optically active amine and the optically active diacyltartaric acid, known are a process wherein a diastereomer salt of (S)-1,2-propanediamine and dibenzoyl-D-tartaric acid is added to 9% hydrochloric acid aqueous solution, to precipitate dibenzoyl-D-tartaric acid which is then recovered by filtration {Japanese Patent No. 2712669 (Example 5)} and a process wherein a diastereomer salt of (S)-1,2-propanediamine and di-p-toluoyl-D-tartaric acid is added to 9% hydrochloric acid aqueous solution, to precipitate di-p-toluoyl-D-tartaric acid which is then recovered by filtration {Japanese Patent No. 2917495 (Example 5)}. However, if these processes are employed as they are, the diacyltartaric acid recovered by solid-liquid separation is likely to be aggregated as a block, and a step of grinding it before recycled use is necessary. Furthermore, if the diacyltartaric acid aggregated as a block is used as it is in an optical resolution step, it takes a long period of time till the salt of an amine and an optically active diacyltartaric acid, essential for optical resolution, is formed. Because of these problems, an optically active diacyl-D-tartaric acid with good properties to allow recycled use cannot be recovered. Moreover, also known is a salt dissociation method wherein the diastereomer salt of (4aR, 8aR)-1-n-propyl-6-oxodecahydro-quinoline and di-p-toluoyl-L-tartaric acid is treated by a diluted sodium hydroxide aqueous solution, and (4aR, 8aR)-1-n-propyl-6-oxodecabydro-quinoline is extracted with methylene chloride, while disodium di-p-toluoyl-L-tartrate is left in the water layer {JP6-70063B (Production Example 1)}. However, the document does not describe any process for recovering di-p-toluoyl-L-tartaric acid from disodium di-p-toluoyl-L-tartrate.

It would therefore be helpful to provide a process for industrially recovering an optically active diacyltartaric acid capable of being easily used in recycling, by dissociating a salt of an amine and the optically active diacyltartaric acid. It would also be helpful to provide a process for recovering an optically active diacyltartaric acid with good properties by dissociating a diastereomer salt of an optically active amine and the optically active diacyltartaric acid, obtained by optical resolution. It would further be helpful to provide a method for recycling the obtained optically active diacyltartaric acid into an optical resolution step.

SUMMARY

We studied intensively on the method for solving the above-mentioned problems, and as a result, arrived at the method disclosed herein. That is, we provide a process for recovering an optically active diacyltartaric acid from a salt of an amine and the optically active diacyltartaric acid in an acid aqueous solution, characterized in that the optically active diacyltartaric acid is added beforehand in the acid aqueous solution. We also provide a process for recovering an optically active diacyltartarc acid, wherein the salt of an amine and the optically active diacyltartaric acid is a diastereomer salt obtained by optically resolving a racemic amine using the optically active diacyltartaric acid. Furthermore, we provide a process for recovering an optically active diacyltartarc acid, comprising an optical resolution step for optically resolving a raw material containing a racemic amine and the optically active diacyltartaric acid and separating the diastereomer salt of an optically active amine and the optically active diacyltartaric acid respectively of one isomer type, a salt dissociation step for dissociating the obtained diastereomer salt into the optically active amine and the optically active diacyltartaric acid using an acid aqueous solution, and a recycling step for recovering the optically active diacyltartaric acid obtained in the salt dissociation step and recycling the recovered optically active diacyltartaric acid into the optical resolution step as a raw material of the optical resolution step, wherein the optically active diacyltartaric acid is added beforehand in the acid aqueous solution used in the salt dissociation step.

DETAILED DESCRIPTION

The salt of an amine and the optically active diacyltartaric acid, used as a raw material, can be any of a salt of an optically inactive amine and the optically active diacyltartaric acid, a diastereomer salt of a racemic amine and the optically active diacyltartaric acid, and a salt of an optically active amine and the optically active diacyltartaric acid. Furthermore, either a crystalline diastereomer salt obtained by optically resolving a racemic amine using an optically active diacyltartaric acid and filtering for separation or a diastereomer salt as an optical antipode contained in the filtered mother liquor can also be used. The optical purity of the amine contained in the salt can be any value. Moreover, the amine is not especially limited, and examples of the optically inactive amine include benzylamine, cyclohexylamine, etc. The racemic amine is not especially limited either. Examples of it include aliphatic amines such as 1,2-diaminopropane, 3-aminobutane, 3-aminopentanenitrile and 2-cyclopropylamino-cyclohexanol, aromatic amines such as α-naphthylethylamine, α-phenylethylamine, 1-methyl-3-phenylpropylamine, α-(p-chlorophenyl)ethylamine and α-(toluylethyl)amine, and heterocyclic amines such as 3-aminopyrrolidine, 3-amino-1-benzylpyrrolidine, and 3-phenyl-1-propyl-piperidine.

Examples of the optically active diacyltartaric acid include benzoic esters such as optically active dibenzoyltartaric acid, optically active di-p-toluoyltartaric acid, optically active di-m-toluoyltartaric acid, optically active di-o-toluoyltartaric acid, optically active dianisoyltartaric acid, optically active di-m-methoxybenzoyltartaric acid and optically active di-o-methoxybenzoyltartaric acid, phenylacetic esters such as optically active diphenylacetyltartaric acid, aliphatic carboxylic esters such as optically active diacetyltartaric acid and optically active dipropionyltartaric acid. Preferred are optically active dibenzoyltartaric acid, optically active di-p-toluoyltartaric acid, optically active di-m-toluoyltartaric acid, optically active di-o-toluoyltartaric acid, optically active dianisoyltartaric acid, optically active di-m-methoxybenzoyltartaric acid and optically active di-o-methoxybenzoyltartaric acid.

In the above, as the diastereomer salt of an amine and a diacyltartaric acid, any combination can be used without any problem. For example:

(1) In the case of optically active dibenzoyltartaric acid, preferred are salts of 1,2-diaminopropane, 3-aminopyrrolidine, 1,2-diaminocyclohexane, α-naphthylethylamine, α-phenylamine, 1-methyl-3-phenylpropylamine, etc.

(2) In the case of optically active di-p-toluoyltartaric acid, preferred are salts of 1,2-diaminopropane, α-(p-chlorophenyl)ethylamine, α-(toluylethyl)amine, 1-methyl-3-phenyl-propylamine, 2-cyclopropylaminocyclohexanol, 3-phenyl-1-propylpiperidine, etc.

(3) In the case of optically active di-p-methoxybenzoyltartaric acid, preferred are salts of 1,2-diaminopropane, 3-aminopentanenitrile, 1-methyl-3-phenylpropylamine, etc.

In the above, an optically active diacyltartaric acid includes both a D-isomer and an L-isomer and means that the optical purity is 98% ee or more.

The acid aqueous solution is not especially limited, and preferred are aqueous solutions of inorganic acids such as hydrochloric acid, sulfuric acid, phosphoric acid and nitric acid. More preferred are hydrochloric acid, sulfuric acid and phosphoric acid aqueous solutions, and especially preferred are hydrochloric acid and sulfuric acid aqueous solutions. The acid concentration is from 2 to 40 wt %. A preferred range is from 5 to 30 wt %, and a more preferred range is from 7 to 20 wt %. The usable amount of the acid is required to be not smaller than an equivalent to the amine contained in the diastereomer salt. A preferred range is from 1.5 to 3.0 equivalents, and a more preferred range is from 1.8 to 2.5 equivalents. Since an optically active diacyltartaric acid is generally a bulky compound, it is preferred to decide the concentration and usable amount of the acid to achieve a concentration of 5 to 15% at which the slurry of the optically active diacyltartaric acid precipitated by salt exchange can be efficiently stirred.

If a salt of an optically active tartaric acid is directly added into the stirred acid aqueous solution, the optically active diacyltartaric acid is precipitated all at once to aggregate a block, and since the optically active tartaric acid salt is also contained in the block, smooth salt exchange does not take place. This method is not preferred either especially in the case where an optically active tartaric acid derivative is used for resolution as a method for industrially producing an optically active amine, since the recovery rate of the optically active amine also declines. Furthermore, if a diastereomer salt is added to a basic aqueous solution of sodium hydroxide or the like, the salt exchange takes place smoothly since the optically active diacyltartaric acid is dissolved as a disodium salt into the aqueous solution. However, if the concentration is lowered to such an extent at which no disodium diacyltartrate is precipitated, it is nessesary to use a large amount of an organic solvent to extract the free optically active amine or to use a halogen-based solvent with a high extracting capability such as chloroform. This is not preferred as an industrial production method with environmental pollution taken into account. Furthermore, since the optically active diacyltartaric acid is hydrolyzed by an alkali, the recovery rate of the optically active diacyltartaric acid declines, and in addition, the chemical purity of the optically active diacyltartaric acid obtained by acidifying the optically active disodium diacyltartrate in an aqueous solution for crystallization and filtering the reaction mixture also declines. These are not preferred for recycled use.

To carry out the salt dissociation smoothly in the acid aqueous solution, the same optically active diacyltartaric acid as that contained in the salt with the amine or in the diastereomer salt with the optically active amine is added into the acid aqueous solution beforehand. The added amount depends on the optically active diacyltartaric acid used and the salt exchange conditions, but it is preferred that the amount is from 0.05 to 3 wt % based on the weight of the acid aqueous solution. An especially preferred range is from 0.1 to 2 wt %. In the case where the rate at which the amine salt or diastereomer salt is added is high, the amount of the optically active tartaric acid added beforehand should be large, and in the case where the rate is low, the salt exchange can smoothly take place even if the added amount is small. It is not preferred that the added amount is too large, since the recycled amount of the recovered optically active diacyltartaric acid is too large to allow efficient production, though the large amount does not cause any problem for salt exchange.

A preferred temperature range of the salt exchange is from 0 to 50° C., and a more preferred range is from 20 to 40° C. If the temperature is in this range, salt exchange can smoothly take place, but a temperature of higher than 50° C. is not preferred, since the precipitated optically active diacyltartaric acid may be molten and likely to form a block, depending on the tartaric acid used, though the salt exchange rate becomes high.

The time necessary for the salt exchange depends on the temperature of salt exchange and the salt used, but usually it is from 1 to 10 hours. Since the amine salt or diastereomer salt is added into the slurry of the optically active diacyltartaric acid added beforehand, it is difficult to identify the situation of salt exchange. However, since the amine salt or diastereomer salt is often different from the optically active tartaric acid in crystal form, the salt exchange situation can be identified if observation is made in detail. To accurately identify the salt exchange situation, a method of determining the amine dissolved in the acid aqueous solution can be employed. Furthermore, in the case where the mother liquor obtained by solid-liquid separation of the intended optically active substance salt in the optical resolution step is used for salt exchange, the salt exchange can take place smoothly if the organic solvent is removed beforehand by means of concentration or the like. Especially it is not preferred that the organic solvent in which the optically active diacyltartaric acid is dissolved is not removed, since the recovery rate of the optically active diacyltartaric acid declines. In the case where the filtered mother liquor is a mixed solution of water and a water-soluble organic solvent, an aqueous solution remaining after removing the organic solvent under reduced pressure beforehand can be used. Furthermore, in the case where the filtered mother liquor is an aqueous solution, it can be used as it is. However, in the case where the concentration of the filtered mother liquor is too low for the salt dissociation step, the mother liquor can be concentrated for adjustment before said diastereomer salt exchange method is employed. Moreover, in the case where the optically active diacyltartaric acid and an inorganic acid or an organic carboxylic acid such as acetic acid are used together in the optical resolution step, the filtered mother liquor contains the acid, but if the acid is soluble in water, the filtered mother liquor can be used as it is in the salt dissociation step as described before. If the acid is not soluble in water, it is contained in the precipitated optically active diacyltartaric acid, but it can be merely changed into a salt when the optically active diacyltartaric acid is recycled into the optical resolution step.

The optically active diacyltartaric acid recovered by salt exchange using the acid aqueous solution containing an optically active diacyltartaric acid is good also in slurry properties. For recovering the precipitated optically active diacyltartaric acid, filtration under reduced pressure, filtration under pressurization or centrifugal liquid extraction can be employed, and the optically active diacyltartaric acid recovered by the method of this invention is also good in filtration properties. The optically active diacyltartaric acid recovered by the method of this invention does not decline in optical purity and is also high in chemical purity.

In the case where the recovered optically active diacyltartaric acid is used as a starting raw material for optical resolution, it can also be dried for recycled use, but if the resolving solvent is water or a hydrous solvent, it can be used as it is for recycled use.

The optical resolution method is not especially limited. For example, a racemic amine and the optically active diacyltartaric acid are mixed in a solvent to synthesize a disastereomer salt and the diastereomer salt is precipitated to allow optical resolution.

EXAMPLES

This disclosure is described below in further detail in reference to examples, but is not limited thereto or thereby.

The optical purity of an optically active diacyltartaric acid was analyzed by means of HPLC equipped with an optical purity analyzing column (CHIRALCEL OJ produced by Daicel Chemical Industries, Ltd.).

The chemical purity was analyzed by means of HPLC equipped with an ODS column.

Example 1

A 300 ml three-neck flask equipped with a stirrer, Dimroth condenser and thermometer was charged with 14.8 g (0.2 mole) of racemic 1,2-diaminopropane, 40.4 g (0.1 mole, optical purity 99.5% ee) of di-p-toluoyl-D-tartaric acid, 170 g of water and 18.8 g (0.18 mole) of 35% hydrochloric acid, and with stirring, the mixture was heated up to 60° C. for dissolution. Then, with stirring, the mixture was cooled to 25° C., for precipitation, and the crystals were collected by filtration to obtain 37.5 g of a diastereomer salt and 203.5 g of a filtered mother liquor. The optical purity of the 1,2-diaminopropane contained in the precipitated diastereomer salt was 76% ee. The obtained diastereomer salt was recrystallized with water, and the crystals were collected by filtration and dried to obtain 20.8 g of a diastereomer salt. The optical purity of the 1,2-diaminopropane contained in the precipitated diastereomer salt was 98.5% ee.

A 300 ml three-neck flask equipped with a stirrer, Dimroth condenser and thermometer was charged with 6.7 g (0.07 mole) of 95% sulfuric acid and 115 g of water, and with stirring at 25 to 30° C., 0.5 g of di-p-toluoyl-D-tartaric acid was added. The mixture was stirred till it became a smooth slurry, when 0.5 g of said diastereomer salt was added, and the mixture was stirred for 10 minutes. It was confirmed that the di-p-toluoyl-D-tartaric acid precipitated due to salt exchange was crystallized, and the remaining 20.3 g of the diastereomer salt was added little by little, taking 1 hour. The mixture was stirred for further 2 hours, to precipitate crystals which were collected by filtration and dried to obtain 17.6 g of d-p-toluoyl-D-tartaric acid. The recovery rate was 98.0%, and the optical purity was 99.5% ee. In neither the optical resolution step nor the salt dissociation step, any racemization occurred concurrently. In HPLC, no impurity peak was detected.

Example 2

A 300 ml four-neck flask equipped with a stirrer, Dimroth condenser, dropping funnel and thermometer was charged with 5.3 g (0.06 mole) of 95% sulfuric acid and 50 g of water, and with stirring at 25 to 30° C., 0.1 g of di-p-toluoyl-D-tartaric acid was added. The mixture was stirred till it became a smooth slurry, when the solution obtained by concentrating 203.5 g of the filtered mother liquor obtained in Example 1 under reduced pressure till the amount became 80 g was slowly added dropwise, taking 2 hours. The mixture was stirred for further 2 hours, to precipitate crystals which were collected by filtration and dried to obtain 13.1 g of di-p-toluoyl-D-tartaric acid. The optical purity was 99.5% ee, and in neither the optical resolution step nor the salt dissociation step, any racemization occurred concurrently. In HPLC, no impurity peak was detected.

Example 3

A 200 ml three-neck flask equipped with a stirrer, Dimroth condenser and thermometer was charged with 4.4 g (0.06 mole) of racemic 1,2-diaminopropane, 11.6 g (0.03 mole, optical purity 99.5% ee) of recovered di-p-toluoyl-D-tartaric acid, 51 g of water and 5.6 g (0.054 mole) of 35% hydrochloric acid, and with stirring, the mixture was heated up to 60° C. for dissolution. Then, with stirring, the solution was cooled to 25° C., to precipitate crystals which were collected by filtration to obtain 11.2 g of a diastereomer salt. The optical purity of the 1,2-diaminopropane contained in the precipitated diastereomer salt was 75% ee. The results were almost the same as those of Example 1.

Example 4

A 2-liter three-neck flask equipped with a stirrer, Dimroth condenser and thermometer was charged with 155.2 g (1.0 mole) of racemic 2-cyclopropylaminocyclohexanol, 270.4 g (0.7 mole, optical purity 99.5% ee) of di-p-toluoyl-D-tartaric acid, 430 g of methanol, 184 g of water and 10.9 g of 35% hydrochloric acid, and the mixture was stirred at 70° C. for 1 hour for dissolution. Then, the mixture was cooled to 50° C., and 0.1 g of seed crystal was added. The mixture was stirred for 30 minutes to precipitate crystals, and was cooled to room temperature, being stirred for further 1 hour. The precipitated crystals were collected by filtration to obtain 258.2 g of a diastereomer salt. The obtained salt was recrystallized with a mixed solvent of 192 g of methanol and 56 g of water, to precipitate and obtain 220.4 g of a diastereomer salt. The optical purity of the 2-cyclopropylaminocyclohexanol contained in the precipitated crystals was 99.0% ee (R-isomer), and as a result of analysis, the purity content was 60.4 g while the yield was 77.8% (in terms of R-isomer). The amount of the contained di-p-toluoyl-D-tartaric acid was found to be 150.2 g as a result of purity analysis.

A 2-liter three-neck flask equipped with a stirrer, Dimroth condenser and thermometer was charged with 900 ml of water and 48.1 g of 95% sulfuric acid, and the mixture was stirred at 25 to 30° C., when 10.0 g of di-p-toluoyl-D-tartaric acid was added. The mixture was stirred for 20 minutes till it became a smooth slurry. Then, with stirring, 1 g of the diastereomer salt was added, and the mixture was stirred for 5 minutes to dissociate the salt with precipitation. It was confirmed that the precipitated di-p-toluoyl-D-tartaric acid became crystal-line, and the remaining diastereomer salt was added, taking about 2 hours. The mixture was stirred for further 4 hours, to precipitate di-p-toluoyl-D-tartaric acid which was isolated using a small centrifugal dehydrator. For rising, 50 g of water was used. The isolated crystals were dried to obtain 155.0 g of di-p-toluoyl-D-tartaric acid. The recovery rate was 96.8%, and the optical purity did not decline. The chemical purity measured by HPLC was also good.

Comparative Example 1 (CPCH/D-PTTA, Direct Salt Dissociation)

A 2-liter three-neck flask equipped with a stirrer, Dimroth condenser and thermometer was charged with 900 ml of water and 81.9 g of 95% sulfuric acid, and the mixture was stirred at 25 to 30° C., when the diastereomer salt obtained as described for Example 4 was added 1 g by 1 g every five minutes. The mixture was stirred for 1 hour, but lumps stuck to the wall of the flask and did not form crystals. Furthermore, the remaining diastereomer salt was added, taking about 2 hours, and the mixture was stirred overnight at room temperature. No crystalline di-p-toluoyl-D-tartaric acid was obtained.

Example 5

A 2-liter three-neck flask equipped with a stirrer, Dimroth condenser and thermometer was charged with the centrifugally dehydrated mother liquor of di-p-toluoyl-D-tartaric acid of Example 4, and the solution was concentrated under reduced pressure at 50 to 60° C., till the amount became about 350 g. The concentrate was cooled to 20 to 30° C., and with stirring, 85 g of 48% sodium hydroxide aqueous solution was added dropwise, to liberate (R)-2-cyclopropylaminocyclohexanol. Then, 300 g of toluene was used to extract twice, and the toluene layer was washed with 60 g of water and concentrated under reduced pressure to obtain 110 g of a concentrate containing 59.8 g of (R)-2-cyclopropylaminocyclohexanol. The concentrate was distilled in vacuum, to obtain 55.3 g of (R)-2-cyclopropylaminocyclohexanol as a fraction of 91-94° C./0.9-1.1 kPa. The optical purity was 99.0% ee, and in neither the salt dissociation step nor the distillation step, the optical purity declined.

Comparative Example 2

A 2-liter three-neck flask equipped with a stirrer, Dimroth condenser and thermometer was charged with 220.4 g of the diastereomer salt obtained in Example 4 {60.4 g (0.39 mole) of (R)-2-cyclopropylaminocyclohexanol and 150.2 g (0.39 mole) of di-p-toluoyl-D-tartaric acid} and 513 ml of water, and the mixture was stirred at 20 to 30° C. Then, 157 g (0.79 mole) of 20% sodium hydroxide aqueous solution was added dropwise, taking about 1 hour, to cause salt dissociation. The aqueous solution was extracted with 600 g of toluene 3 times, but the recovery rate of (R)-2-cyclopropylaminocyclohexanol was as low as 56%. The water layer as extraction residue was adjusted to lower than pH 1 using 95% sulfuric acid, and the crystals precipitated were collected by filtration. The chemical purity of di-p-toluoyl-D-tartaric acid was about 93%, and it contained p-toluic acid produced by hydrolysis.

Example 6

A 300 ml three-neck flask equipped with a stirrer, Dimroth condenser and thermometer was charged with 5.0 g (0.07 mole) of racemic 1,2-diaminopropane, 25.6 g (0.07 mole, optical purity 99.4% ee) of dibenzoyl-L-tartaric acid monohydrate and 100 g of water, and the mixture was stirred while being heated up to 60° C. for dissolution. Then, with stirring, the mixture was cooled to 25° C., to cause precipitation, and the crystals were collected by filtration and dried to obtain 12.8 g of a diastereomer salt. The optical purity of the 1,2-diaminopropane contained in the precipitated diastereomer salt was 92.5% ee, and the amount of dibenzoyl-L-tartaric acid was 10.6 g.

A 300 ml three-neck flask equipped with a stirrer, Dimroth condenser and thermometer was charged with 91 g of 4% hydrochloric acid aqueous solution, and with stirring at 25 to 30° C., 1 g of dibenzoyl-L-tartaric acid was added. The mixture was stirred till it became a smooth slurry, when 0.5 g of said diastereomer salt was added. The mixture was stirred for 10 minutes to dissociate the salt with precipitation, and it was confirmed that the precipitated dibenzoyl-L-tartaric acid was crystallized. Then, the remaining diastereomer salt was added little by little taking 1 hour. The mixture was stirred for further 2 hours, to precipitate crystals which were collected by filtration and dried to obtain 10.9 g of dibenzoyl-L-tartaric acid. The recovery rate was 94.0%. The optical purity was 99.4% ee, and in neither the optical resolution step nor the salt dissociation step, any racemization occurred concurrently. By HPLC, no impurity peak was detected.

Example 7

A 500 ml three-neck flask equipped with a stirrer, Dimroth condenser and thermometer was charged with 200 g of 5% sulfuric acid aqueous solution, and with stirring at 25 to 30° C., 1 g of dianisoyl-L-tartaric acid (optical purity 99.6% ee) was added. The mixture was stirred, and into the solution, 1 g of the salt of aminopentanenitrile and dianisoyl-L-tartaric acid (optical purity 99.6% ee) was added. The mixture was stirred for about 10 minutes till it became a smooth slurry. It was confirmed that the dianisoyl-L-tartaric acid precipitated due to salt exchange was crystallized, and 48.7 g (0.1 mole in total) of the salt of aminopentanenitrile and dianisoyl-L-tartaric acid (optical purity 99.6% ee) was added, taking about 1 hour. The mixture was stirred for further 2 hours, to precipitate crystals which were collected by filtration and dried to obtain 42.8 g of dianisoyl-L-tartaric acid. The recovery rate was 97.8%, and the optical purity was 99.6% ee. In the salt dissociation step, no racemization occurred concurrently.

Example 8

As described for Example 7, 50.4 g of the salt of 3-aminopyrrolidine and dianisoyl-L-tartaric acid (optical purity 99.6% ee) was used for salt exchange, to obtain 41.3 g of dry dianisoyl-L-tartaric acid. The recovery rate was 94.3%, and the optical purity was 99.6% ee. In the salt dissociation step, no racemization occurred concurrently.

Example 9

As described for Example 7, 52.5 g of the salt of benzylamine and dianisoyl-L-tartaric acid (optical purity 99.6% ee) was used for salt exchange, to obtain 42.3 g of dry dianisoyl-L-tartaric acid. The recovery rate was 96.6%, and the optical purity was 99.6% ee. In the salt dissociation step, no racemization occurred concurrently.

INDUSTRIAL APPLICABILITY

An optically active diacyltartaric acid used as an optical resolving agent for optically resolving a racemic amine can be efficiently recovered. The recovered optically active diacyltartaric acid can be reused as a resolving agent for production of an optically active amine.

The invention claimed is:

1. An industrial process for recovering an optically active diacyltartaric acid from a salt of an amine and the optically active diacyltartaric acid in an acid aqueous solution, comprising the step that the optically active diacyltartaric acid is added beforehand in the acid aqueous solution and a recycling step wherein 94% to 98% of the optically active diacyltartaric acid is recovered.

2. The process according to claim 1, wherein the salt of an amine and the optically active diacyltartaric acid is a diastereomer salt obtained by optically resolving a racemic amine using the optically active diacyltartaric acid.

3. The process according to claim 1, wherein the temperature of the acid aqueous solution is from 0 to 50° C.

4. The process according to claim 1, wherein the optically active diacyltartaric acid is an optically active dibenzoyltartaric acid, optically active ditoluoyltartaric acid, or optically active dimethoxybenzoyltartaric acid.

5. The process according to claim 1, wherein the added amount of the optically active diacyltartaric acid is from 0.05 to 3 wt % based on the weight of the acid aqueous solution.

6. The process according to claim 1, wherein the acid aqueous solution is an aqueous solution of an inorganic acid.

7. An industrial process for recovering an optically active diacyltartaric acid, comprising:
an optical resolution step for optically resolving a raw material composition containing a racemic amine and the optically active diacyltartaric acid;
separating the diastereomer salt of one isomer of the optically active amine and the optically active diacyltartaric acid;
a salt dissociation step for dissociating the obtained diastereomer salt into the optically active amine and the optically active diacyltartaric acid using an acid aqueous solution; and
a recycling step to recover 94% to 98% of the optically active diacyltartaric acid obtained in the salt dissociation step and recycling the recovered optically active diacyltartaric acid into the optical resolution step as a raw material of the optical resolution step, wherein the optically active diacyltartaric acid is added beforehand in the acid aqueous solution used in the salt dissociation step.

8. An industrial process for recovering an optically active diacyltartaric acid comprising:
contacting an amine and the optically active diacyltartaric acid and an acid aqueous solution;
precipitating a diastereomer salt of the amine and the optically active diacyltartaric acid;
contacting the diastereomer salt with an acid aqueous solution and the optically active diacyltartaric acid;
precipitating the optically active diacyltarteric acid; and
recovering 94% to 98% of the optically active diacyltartaric acid and recycling same for use in the process.

9. The process according to claim 8, wherein the salt of an amine and the optically active diacyltartaric acid is a diastereomer salt obtained by optically resolving a racemic amine using the optically active diacyltartaric acid.

10. The process according to claim 8, wherein the temperature of the acid aqueous solution is from 0 to 50° C.

11. The process according to claim 8, wherein the optically active diacyltartaric acid is an optically active dibenzoyltartaric acid, optically active ditoluoyltartaric acid, or optically active dimethoxybenzoyltartaric acid.

12. The process according to claim 8, wherein the added amount of the optically active diacyltartaric acid is from 0.05 to 3 wt % based on the weight of the acid aqueous solution.

13. The process according to claim 8, wherein the acid aqueous solution is an aqueous solution of an inorganic acid.

14. An industrial process for recovering an optically active diacyltartaric acid comprising:
contacting an amine and the optically active diacyltartaric acid and water;
precipitating a diastereomer salt of the amine and the optically active diacyltartaric acid;
contacting the diastereomer salt of the amine and the optically active diacyltartaric acid with an aqueous acid solution and optically active diacyltartaric acid;
precipitating the optically active diacyltartaric acid; and
recovering 94% to 98% of the optically active diacyltartaric acid and recycling same for use in the process.

15. The process according to claim 14, wherein the salt of an amine and the optically active diacyltartaric acid is a diastereomer salt obtained by optically resolving a racemic amine using the optically active diacyltartaric acid.

16. The process according to claim 14, wherein the temperature of the acid aqueous solution is from 0 to 50° C.

17. The process according to claim 14, wherein the optically active diacyltartaric acid is an optically active dibenzoyltartaric acid, optically active ditoluoyltartaric acid, or optically active dimethoxybenzoyltartaric acid.

18. The process according to claim 14, wherein the added amount of the optically active diacyltartaric acid is from 0.05 to 3 wt % based on the weight of the acid aqueous solution.

19. The process according to claim 14, wherein the acid aqueous solution is an aqueous solution of an inorganic acid.

20. An industrial process for recovering an optically active diacyltartaric acid comprising:
contacting a salt of an amine and the optically active diacyltartaric acid with an acid aqueous solution and the optically active diacyltartaric acid;
precipitating the optically active diacyltartaric acid;
adding further a diastereomer salt of the amino acid and the optically active diacyltartaric acid; and
precipitating the optically active diacyltartaric acid; and
recovering 94% to 98% of the optically active diacyltartaric acid and recycling same for use in the process.

21. The process according to claim 20, wherein the salt of an amine and the optically active diacyltartaric acid is a diastereomer salt obtained by optically resolving a racemic amine using the optically active diacyltartaric acid.

22. The process according to claim 20, wherein the temperature of the acid aqueous solution is from 0 to 50° C.

23. The process according to claim 20, wherein the optically active diacyltartaric acid is an optically active dibenzoyltartaric acid, optically active ditoluoyltartaric acid, or optically active dimethoxybenzoyltartaric acid.

24. The process according to claim 20, wherein the added amount of the optically active diacyltartaric acid is from 0.05 to 3 wt % based on the weight of the acid aqueous solution.

25. The process according to claim 20, wherein the acid aqueous solution is an aqueous solution of an inorganic acid.

* * * * *